(12) United States Patent
Chae et al.

(10) Patent No.: US 9,957,280 B2
(45) Date of Patent: May 1, 2018

(54) LUMINESCENT COMPOUND AND ELECTROLUMINESCENT DEVICE EXHIBITING THERMALLY ACTIVATED DELAYED FLUORESCENCE

(71) Applicants: Samsung Electronics Co., Ltd., Suwon si, Gyeonggi-Do (KR); Massachusetts Institute of Technology, Cambridge, MA (US)

(72) Inventors: Hyun Sik Chae, Cambridge, MA (US); David P. McMahon, Cambridge, MA (US); Troy Van Voorhis, Cambridge, MA (US); Ohyun Kwon, Seoul (KR); Seong Ik Hong, Newton, MA (US); Soonok Jeon, Seoul (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 264 days.

(21) Appl. No.: 14/667,617

(22) Filed: Mar. 24, 2015

(65) Prior Publication Data

US 2016/0168162 A1    Jun. 16, 2016

Related U.S. Application Data

(60) Provisional application No. 62/092,132, filed on Dec. 15, 2014.

(51) Int. Cl.
| | |
|---|---|
| *C07D 491/147* | (2006.01) |
| *H01L 51/00* | (2006.01) |
| *H01L 51/50* | (2006.01) |
| *H01L 51/52* | (2006.01) |

(52) U.S. Cl.
CPC ...... *C07D 491/147* (2013.01); *H01L 51/0071* (2013.01); *H01L 51/0072* (2013.01); *H01L 51/5088* (2013.01); *H01L 51/5092* (2013.01); *H01L 51/5203* (2013.01)

(58) Field of Classification Search
CPC .................................................. C07D 491/147
See application file for complete search history.

(56) References Cited

U.S. PATENT DOCUMENTS

| | | | |
|---|---|---|---|
| 8,168,307 B2 | 5/2012 | Iida et al. | |
| 8,435,679 B2 | 5/2013 | Lamanna et al. | |
| 8,643,268 B2 | 2/2014 | Ogiwara et al. | |
| 9,219,242 B2 | 12/2015 | Ogiwara et al. | |
| 9,276,228 B2 | 3/2016 | Seo et al. | |
| 9,328,097 B2 | 5/2016 | Xu et al. | |
| 2010/0187984 A1* | 7/2010 | Lin | C07D 491/04 313/504 |
| 2010/0327265 A1 | 12/2010 | Kimura et al. | |
| 2015/0270494 A1 | 9/2015 | Ku et al. | |
| 2015/0280158 A1 | 10/2015 | Ogiwara et al. | |
| 2016/0093813 A1 | 3/2016 | Stoessel et al. | |
| 2016/0168162 A1 | 6/2016 | Chae et al. | |
| 2016/0181529 A1 | 6/2016 | Tsai et al. | |
| 2016/0181545 A1 | 6/2016 | Stoessel et al. | |

FOREIGN PATENT DOCUMENTS

| | | |
|---|---|---|
| KR | 20130117534 A | 10/2013 |
| WO | 2010090925 A1 | 8/2010 |
| WO | 2015108049 A1 | 7/2015 |
| WO | 2016116517 A1 | 7/2016 |

\* cited by examiner

*Primary Examiner* — Kuo-Liang Peng
(74) *Attorney, Agent, or Firm* — Cantor Colburn LLP

(57) ABSTRACT

A chemical compound is provided having a structure that includes at least one donor moiety covalently bonded to at least one acceptor moiety. For example, the compound may include an indolocarbazole moiety covalently bonded to at least one furylpyridine moiety. The compound may exhibit thermally activated delayed fluorescence and an accompanying $\Delta E_{ST}$ of no greater than about 0.25 eV. The compound finds use in OLED display technology.

25 Claims, 14 Drawing Sheets

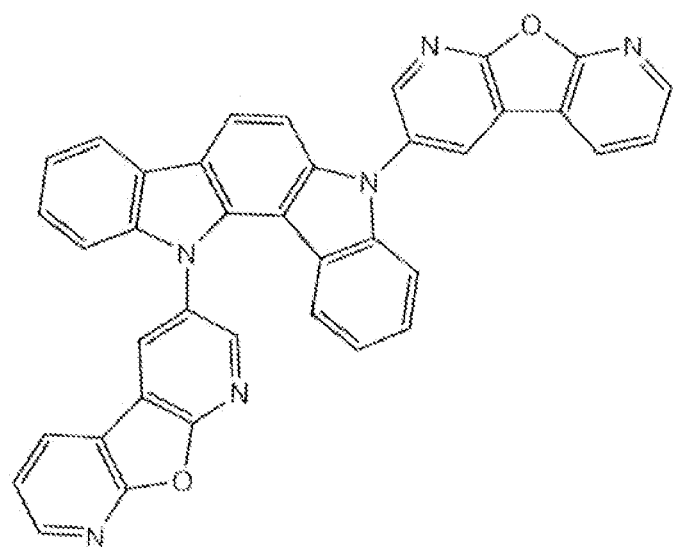
FIG. 3A (Compound 1)
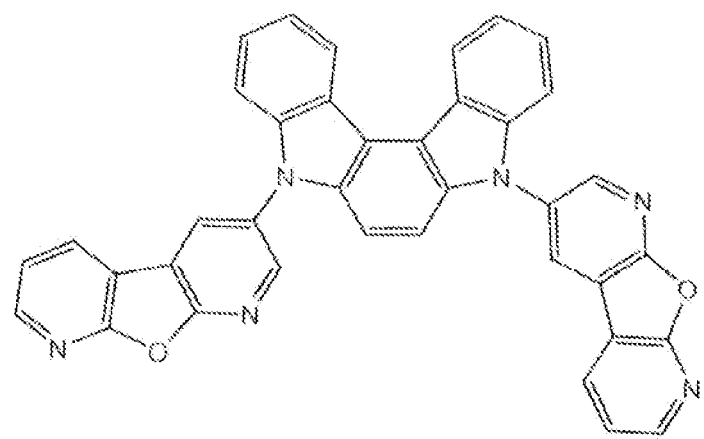
FIG. 3B (Compound 2)

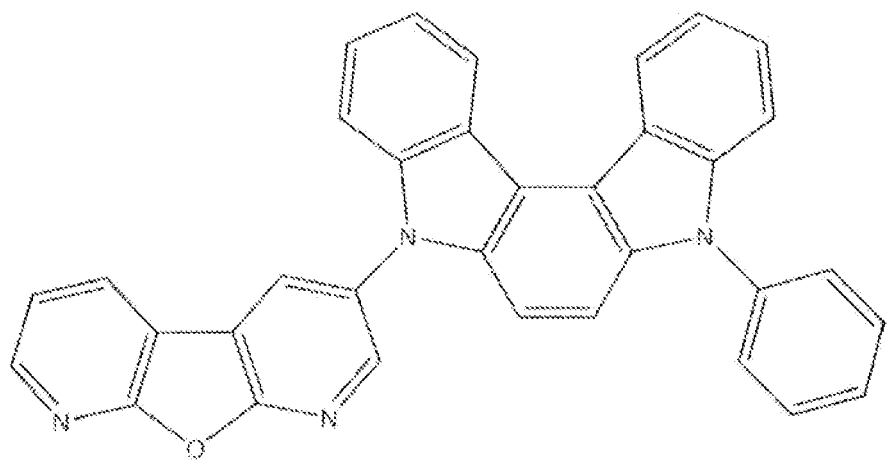
FIG. 3C (Compound 3)
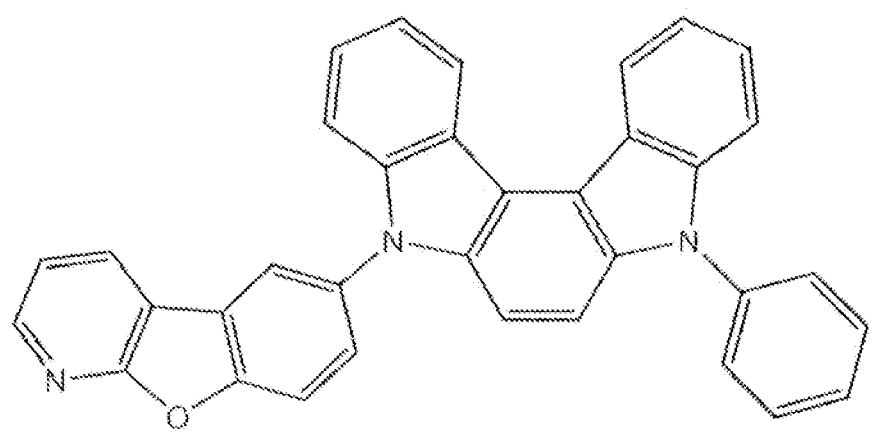
FIG. 3D (Compound 4)

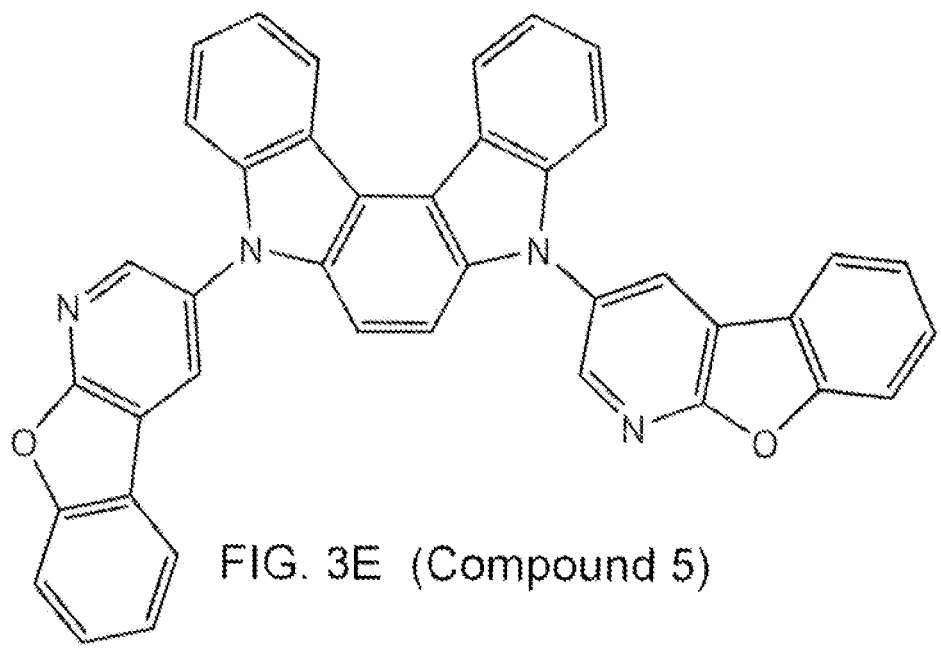
FIG. 3E (Compound 5)
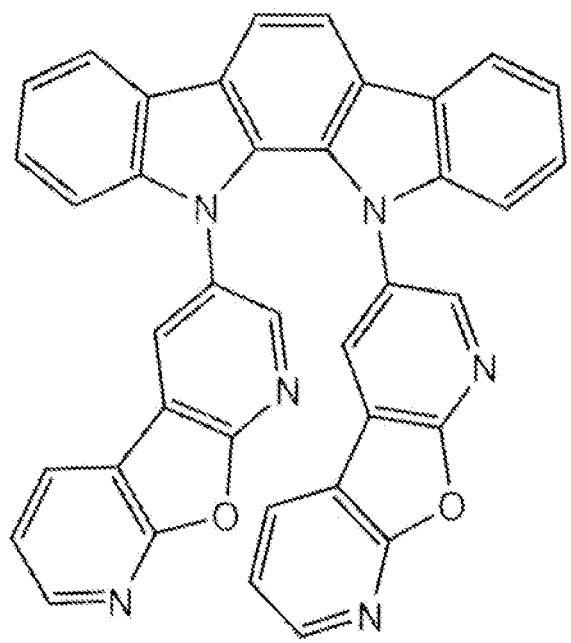
FIG. 3F (Compound 6)

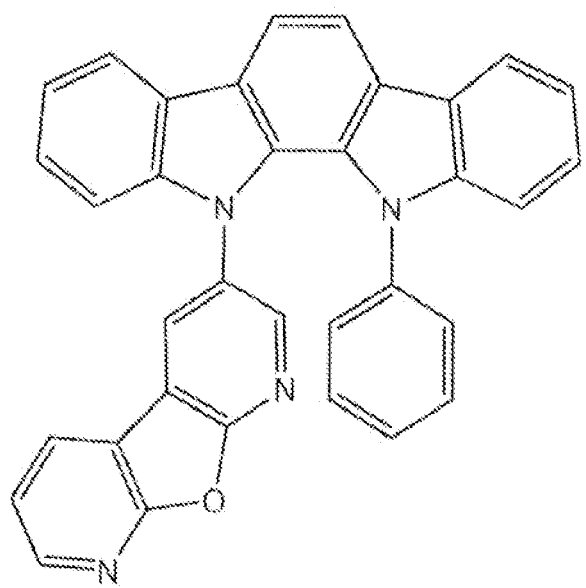
FIG. 3G (Compound 7)
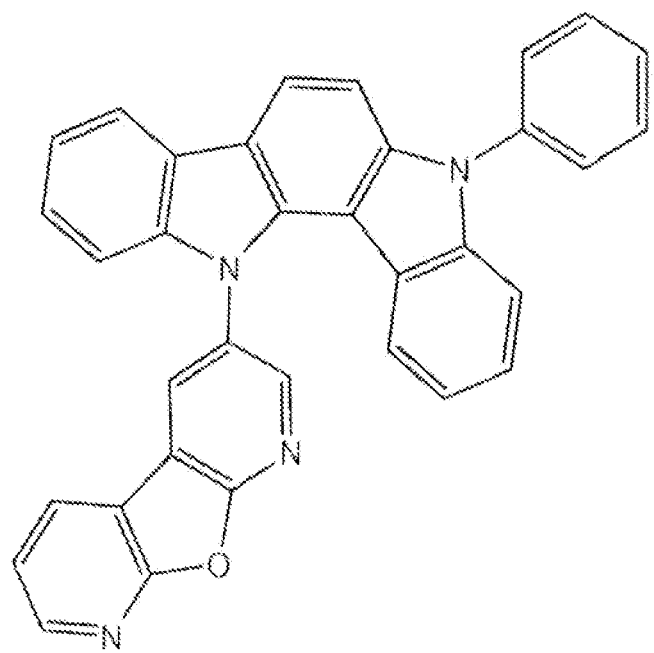
FIG. 3H (Compound 8)

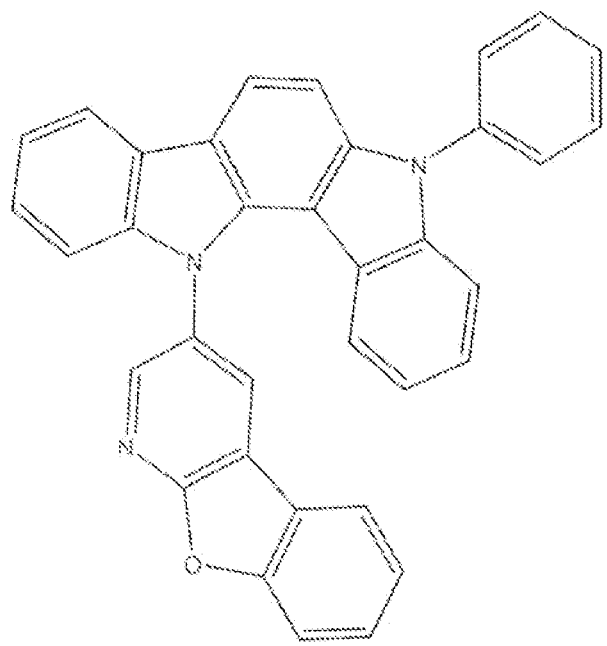
FIG. 3I (Compound 9)
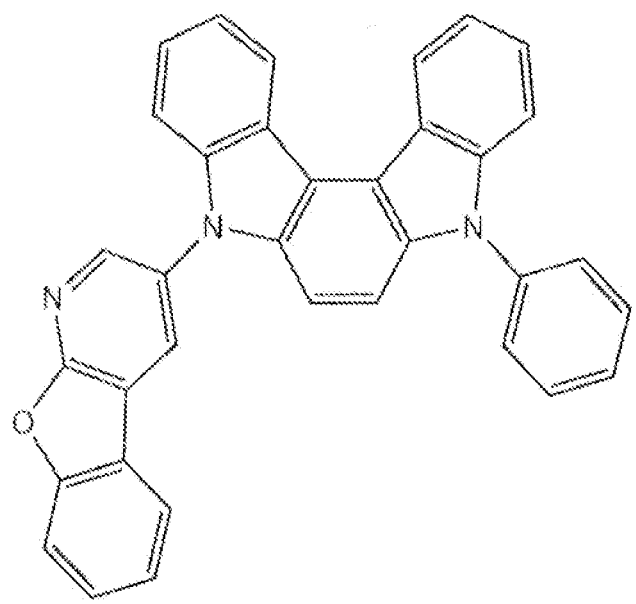
FIG. 3J (Compound 10)

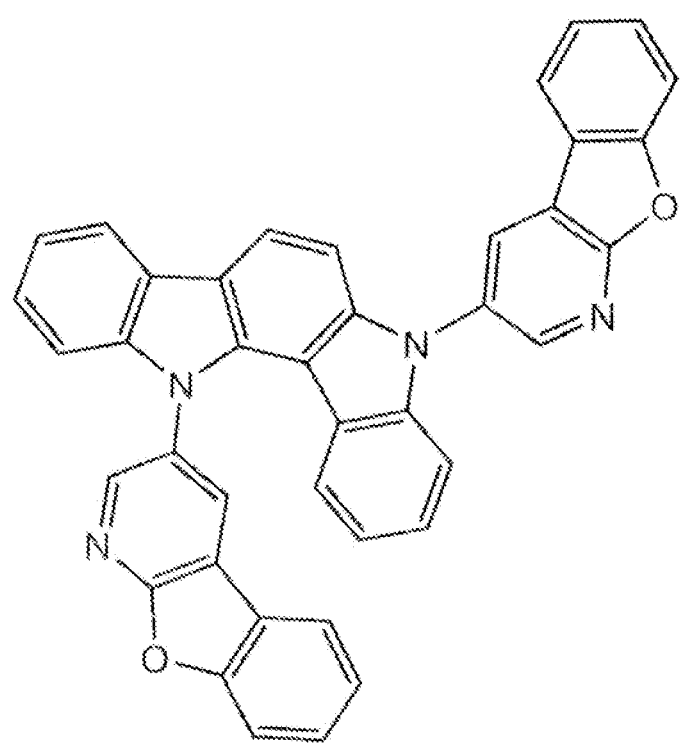
FIG. 3K (Compound 11)

Adv. Mater. 2013, 25(4), 596

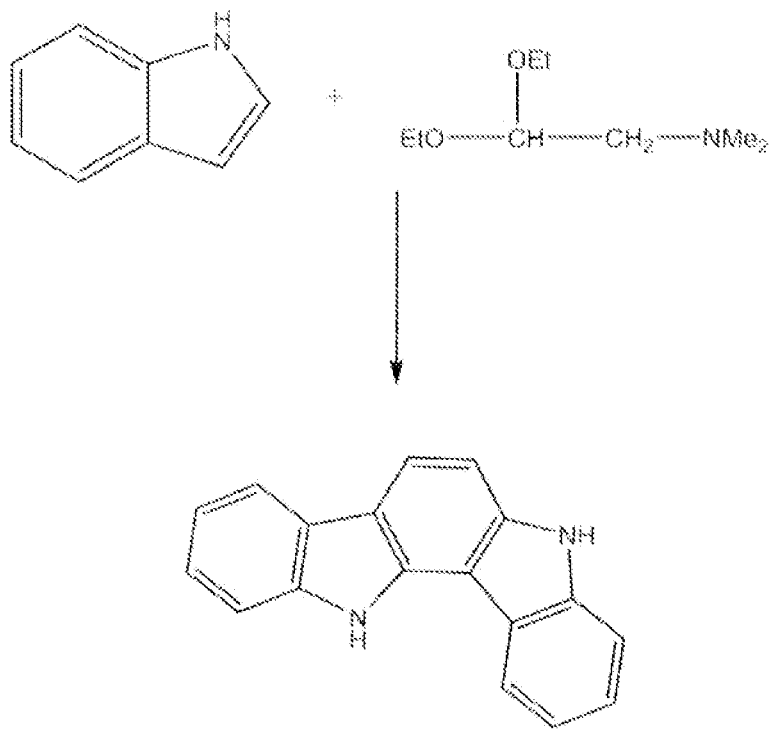
FIG. 4B Commercially available or reported synthetic routes
WO2011049063A1
WO2010113755A1
Synthetic Communications 2000, 30 (20), 3651
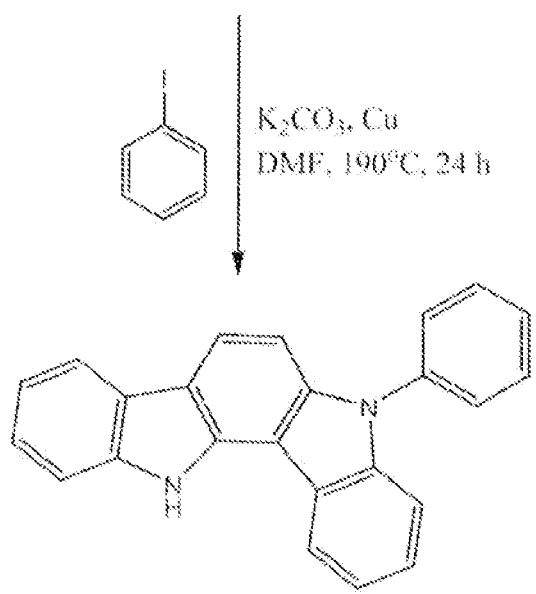

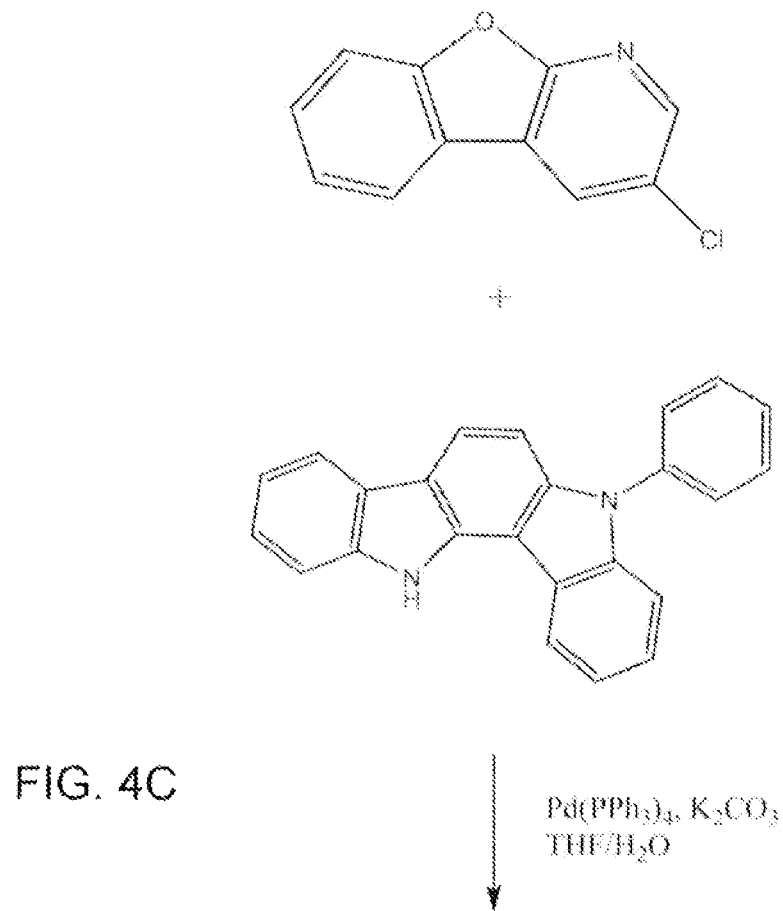
FIG. 4C
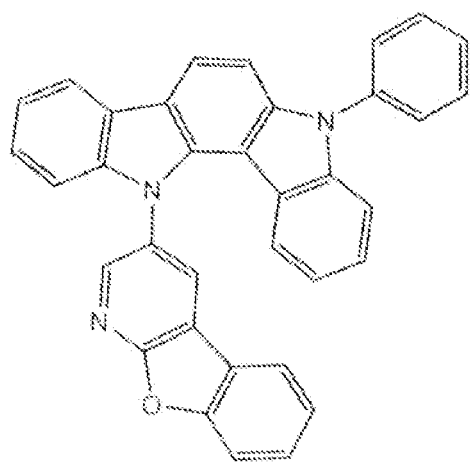

| Comp | S₁ (eV) | T₁ (eV) | ΔE$_{ST}$ | f | HOMO (eV) | LUMO (eV) | Eg (eV) |
|---|---|---|---|---|---|---|---|
| 1 | 2.87 (432nm) | 2.77 | 0.1 | 0.013 | 5.33 | 1.99 | 3.34 |
| 2 | 2.8 (443nm) | 2.7 | 0.1 | 0.017 | 5.2 | 1.93 | 3.27 |
| 3 | 2.7 (459nm) | 2.62 | 0.08 | 0.010 | 5.03 | 1.88 | 3.15 |
| 4 | 2.94 (422nm) | 2.75 | 0.20 | 0.0065 | 4.93 | 1.55 | 3.37 |
| 5 | 2.96 (419nm) | 2.76 | 0.20 | 0.0062 | 5.09 | 1.61 | 3.48 |
| 6 | 2.95 (420nm) | 2.83 | 0.11 | 0.053 | 5.44 | 1.96 | 3.48 |
| 7 | 2.94 (422nm) | 2.82 | 0.11 | 0.0017 | 5.25 | 1.80 | 3.46 |
| 8 | 2.78 (446nm) | 2.70 | 0.08 | 0.012 | 5.14 | 1.88 | 3.26 |
| 9 | 3.0 (413nm) | 2.88 | 0.115 | 0.017 | 5.09 | 1.58 | 3.51 |
| 10 | 2.91 (426 nm) | 2.75 | 0.16 | 0.003 | 4.98 | 1.55 | 3.43 |
| 11 | 3.05 (407nm) | 2.92 | 0.126 | 0.0175 | 5.2 | 1.63 | 3.56 |

Note: f: oscillation strength factor
    S₁: singlet energy
    T₁: triplet energy
    ΔEST : energy difference between singlet and triplet
    HOMO: highest occupied molecular orbital
    LUMO: lowest unoccupied molecular orbital
    E$_g$(eV): band gap = HOMO-LUMO

- All showed very desired TADF characteristics; small ΔE$_{ST}$
- They exhibit blue and/or sky-blue emission as emitter in OLED

FIG. 5

LUMINESCENT COMPOUND AND ELECTROLUMINESCENT DEVICE EXHIBITING THERMALLY ACTIVATED DELAYED FLUORESCENCE

TECHNICAL FIELD

Provided generally are luminescent compounds that may be used in electroluminescent devices. The compounds may exhibit thermally activated delayed fluorescence (TADF).

BACKGROUND

Electroluminescent devices represent an important current and future product in the electronic display industry. Such devices may be constructed in a configuration comprising an electroluminescent material positioned in electronic communication with electron-injection and hole-injection electrodes. When a voltage is applied to the electrodes, holes and electrons are injected into the electroluminescent material from the hole-injection and electron-injection electrodes, respectively. Once the holes and electrons are combined in the electroluminescent material, light is emitted.

OLED is an acronym for an organic light-emitting diode in which an organic emissive electroluminescent (EL) material may be applied as a layer, the layer emitting light in response to an electric potential or current. Two major areas of research in OLED are solid state lighting and display application. In recent years, devices containing organic light emitting diodes (OLED) have been proposed that use organic compounds such as perylenes, thiazole derivatives, quinacridone derivatives, rubrenes, benzophenone derivatives, and coumarin derivatives. However, conventional fluorescent organic compounds typically exhibit a low luminous efficiency. Exciton production efficiency is limited to about 25% due to the deactivation of triplet excitons. When used in an organic EL element, the luminescent efficiency is at most about 5%.

High color purity and long operational lifetimes for deep blue display applications have been problematic in traditional OLED devices for several decades. Therefore, development of efficient and operation stable blue OLED would dramatically impact on the success of display and light applications.

Recently, devices exhibiting TADF have demonstrated highly efficient EL performance, exceeding over 19% of external quantum efficiency. One main strategy in material design for TADF involves incorporating donor and acceptor units together in an orthogonal fashion to separate highest occupied molecular orbitals (HOMO) from lowest unoccupied molecular orbitals (LUMO), thereby leading to small orbital overlap between HOMO and LUMO. This results in a small energy gap between singlets and triplets, allowing a reverse intersystem crossing (RISC) to occur to provide a highly efficient OLED.

It is known that certain porphyrin-based metal complex may be used as a fluorescent organic compound as a light-emitting material for the organic EL element. In such a case, the porphyrin-based metal complex may exhibit TADF. Additional TADF compounds are known in the art as well.

Nevertheless, opportunities exist to provide alternatives to known TADF compounds and to improve known electroluminescent display technologies.

SUMMARY

A compound is provided of a structure that includes an indolocarbazole moiety covalently bonded to at least one furylpyridine moiety. For example, the compound may have the following structure wherein: the indolocarbozole moiety is represented by formula (1),

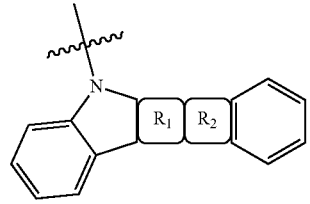

(1)

ring $R_1$ is represented by formula (1a) and is fused to an adjacent heterocycle,

(1a)

ring $R_2$ is represented by formula (1b) and is fused to an adjacent aromatic ring, and

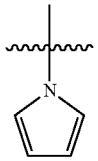

(1b)

rings $R_1$ and $R_2$ are fused together. The compound may be provided in a luminescent material located as a part of an electroluminescent device. The compound may exhibit a $\Delta E_{ST}$ (energy difference between a singlet state and a triplet state) of no greater than about 0.25 eV. Preferably, $\Delta E_{ST}$ is no greater than about 0.20 eV. Optimally $\Delta E_{ST}$ is no greater than about 0.10 eV.

In another embodiment, a thermally activated delayed fluorescent compound is provided of a structure that includes a donor moiety covalently bonded to at least one furylpyridine acceptor moiety. Various donor moieties known in the art may be employed, e.g., an indolocarbazole moiety. The compound exhibits a $\Delta E_{ST}$ of no greater than about 0.25 eV.

Other embodiments of the invention will be apparent to those of ordinary skill in the art in view of the disclosure contained herein.

BRIEF DESCRIPTION OF THE DRAWINGS

FIGS. 2A and 2B collectively show the difference between fused toluene rings (FIG. 2A) and toluene rings that are covalently bonded but not fused together (FIG. 2B). FIG. 2C depict a simple exemplary indolocarbazole, wherein rings $R_6$, $R_7$, and $R_8$ are aromatic and optionally heterocyclic in nature. FIG. 2D depicts an exemplary simple furylpyridine.

FIGS. 3A-3K, collectively referred to as FIG. 3, depict various embodiments of the inventive compound that have been evaluated for their luminescent properties.

FIGS. 4A-4C, collectively referred to as FIG. 4, depict in step-by-step sequence how an exemplary compound (Compound 9) may be chemically synthesized in a step-by-step manner. FIG. 4A shows how an acceptor for Compound 9 may be formed. FIG. 4B shows how a donor for Compound 9 may be formed. FIG. 4C shows how the acceptor of FIG. 4A and the donor of FIG. 4B may be joined to form Compound 9.

FIG. 5 is a table that shows energy calculations associated with the compounds of FIG. 3.

DESCRIPTION

Overview and Definitions

Figure 1:
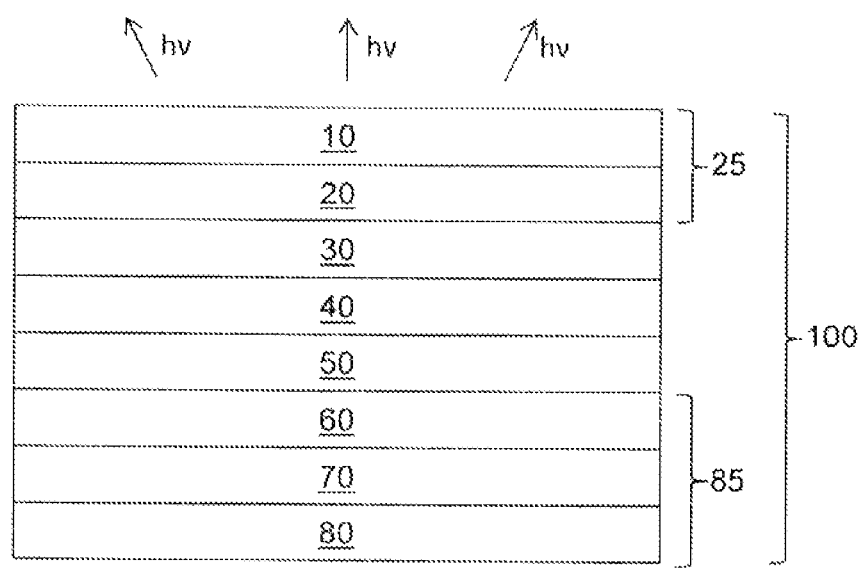
FIG. 1 schematically depicts in simplified format an exemplary architecture of an electroluminescent device emitting light in the form of hv.

Provided generally are luminescent compounds that may be used in electroluminescent devices. The compounds may exhibit thermally activated delayed fluorescence and high luminescent efficiency associated therewith. While the compounds may exhibit luminescence in a blue wavelength, the luminescent compounds are well suited for OLED applications, e.g., in which electronic displays are provided having blue, green, and red pixels.

Before describing the invention in detail, it is to be understood that the invention is not generally limited to specific electrode materials or device configurations, as such may vary. It is also to be understood that the terminology used herein is intended to describe particular embodiments only, and is not intended to be limiting.

Furthermore, as used in this specification and the appended claims, the singular article forms "a," "an," and "the" include both singular and plural referents unless the context clearly dictates otherwise. Thus, for example, reference to "a moiety" includes a plurality of moieties and a single moiety, reference to "an electrode" includes a single electrode as well as a collection of electrodes, reference to "a chemical compound" includes one or more chemical compounds regardless whether the compounds are identical, similar, or different, and the like.

In this specification and in the claims that follow, reference is made to a number of terms that are defined to have the following meanings, unless the context in which they are employed clearly indicates otherwise:

The term "chemical compound" is used in its ordinary sense and refers a combination of two or more elements in the periodic table, without regard to how the elements are bonded together, e.g., via covalent, ionic, metallic, or some other type of bonds. Covalent bonds may be single, double, or triple in nature.

The term "derivative" as in an "indolocarbazole derivative" is used herein in its chemical sense, e.g., to indicate that the structure of indolocarbazole may be modified to include one or more substituents where a particular atom or moiety may ordinarily be located. For example, an indolocarbazole derivative may include a halogen atom, an alkyl group, or a benzyl group in place of a hydrogen or hydrido. In addition, when a chemical moiety is recited in the claims that follow this specification, recitation of the moiety is understood to encompass one or more derivatives thereof to an extent that does not substantially hinder the operability of the invention.

The term "donor moiety" is used in its ordinary electronic sense and refers to a moiety that donates an electron or accepts a hole. As a related matter, the term "acceptor" as applied to "moiety" is used to refer to a moiety that accepts an electron or donates a hole.

The term "electroluminescent" is used herein to describe a compound, material and/or a device that emits electromagnetic radiation upon application of an electrical potential and/or current. When electrons and holes are injected into an electroluminescent material, light is emitted upon the combination of the electrons and holes, thereby resulting in electroluminescence.

The terms "electronic," "electronically," and the like are used in their ordinary sense and relate to structures, e.g., semiconductor microstructures, that provide controlled conduction of electrons holes, or other charge carriers. The term "electronic communication" is used herein to refer to a connection between two bodies that permits a flow of current, i.e., transfer of electrons or holes from one body to the other, e.g., for combination. The term "electronic communication" usually but does not necessarily imply direct mechanical contact between the two bodies.

The terms "fluorescent," "fluorescence," and the like refer to a luminescent phenomenon in which emitted fluorescent light has a longer wavelength and lower energy than the absorbed light.

Figure 2A:
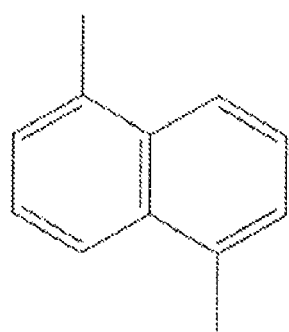
FIGS. 2A-2D, collectively referred to as FIG. 2, depict various chemical moieties and pertinent variants thereof and how they relate to each other.
Figure 2B:
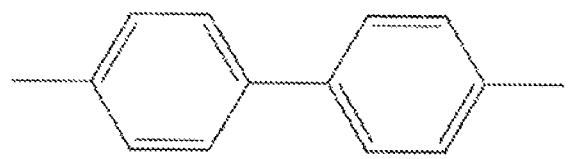

The term "fused" as in "fused rings" is used herein to describe the chemical structure of rings and how they relate to each other, e.g., as depicted in FIGS. 2A and 2B, regardless of the ring structures' relative angular orientation.

The term "emission modifier" refers to a compound that alters the emission spectrum of an electroluminescent material. The emission modifier may be itself an electroluminescent or luminescent material.

Figure 2C:
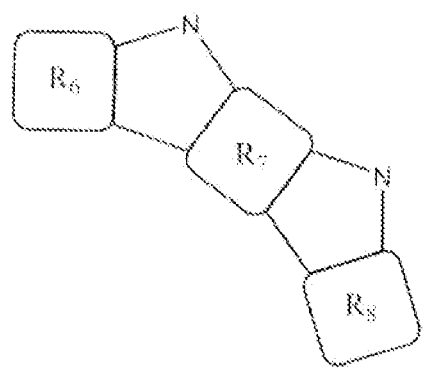

The term "indolocarbazole" as in a "indolocarbazole moiety" is used in its ordinary sense and may refer to a compound having a general structure of as shown in FIG. 2C, wherein rings $R_6$, $R_7$, and $R_8$ are aromatic. At a minimum, the chemical structure of indolocarbazole includes an aromatic ring, such as a benzene ring, fused to a five-member heterocycle, wherein the heterocycle optionally includes nitrogen. More typically, the structure includes a five-member heterocycle, fused to two or more aromatic rings. Additional indolocarbazole compounds, moieties, and variants thereof are known in the art and/or described herein.

Figure 2D:
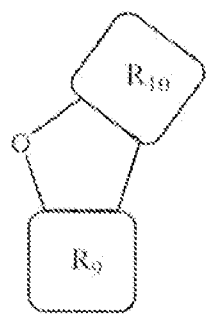

The term "furylpyridine" as in a "furylpyridine moiety" is used in its ordinary sense and may refer to a compound having a general structure as shown in FIG. 2D, wherein rings $R_9$ and $R_{10}$ are independently selected from heterocycles, aryls groups, benzyl groups, and pyridines. At a minimum, a furylpyridine typically includes a furan fused to a pyridine. Additional furylpyridine compounds, moieties, and variants thereof are known in the art and/or described herein. Optionally, one or more rings shown in FIG. 2D may be absent or replaced with hydrogen.

The terms "heterocycle," "heterocyclic," and the like are used in their ordinary chemical sense and refer to a ring of atoms of at least two elements, one element of which typically being a carbon.

The terms "luminescent," "luminescence," and the like are used herein in their ordinary sense and refer typically to something that emits cold body radiation. The terms are distinguishable from incandescence, a phenomenon in which is light emitted by a substance as a result primarily of heating.

The term "moiety" is used herein in its ordinary chemical sense and refers to a part or a functional group of a molecule. In some instances, a moiety may have a structure that encompasses the entire molecule. In such a case, as a matter of nomenclature convention, the molecule may be named without explicit recitation of the term "moiety."

"Optional" or "optionally" means that the subsequently described event or circumstance may or may not occur, and that the description includes instances where said event or circumstance occurs and instances where it does not. For example, an electroluminescent device comprising an "optional layer" means that the layer may or may not be present and that the description includes either state.

The terms "red," "green," and "blue" are used in their ordinary sense and are used in reference to an additive color model in which red, green, and blue light are added together in various ways to reproduce a broad array of colors in a display.

The term "singlet" is used as understood by a chemist to refer to a molecular electronic state with total spin, S=0. Likewise, the term "triplet" refers to a state with total spin, S=1.

Exemplary Compound

Provided is a chemical compound of a structure that includes at least one donor moiety covalently bonded to at least one acceptor moiety. In a first embodiment, a compound is provided that includes an indolocarbazole moiety covalently bonded to at least one furylpyridine moiety. The indolocarbozole moiety may be bonded via a nitrogen thereof to at least one furylpyridine moiety. For example, the furylpyridine moiety may be a furylmonopyridine or a furylbipyridine. In the case of furylbipyridine, the indolocarbozole moiety may be bonded via nitrogens thereof to furylpyridine moieties.

As discussed above, the indolocarbozole moiety may be generally represented by formula (1). In particular, the following indolocarbazole moieties represented by formulae (1.1), (1.2), (1.3), (1.4), and (1.5), are specific embodiments of the indolocarbozole moiety represented by formula (1).

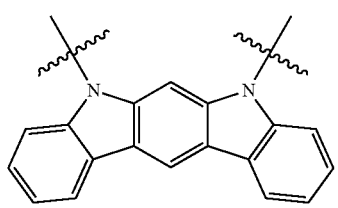

(1.1)

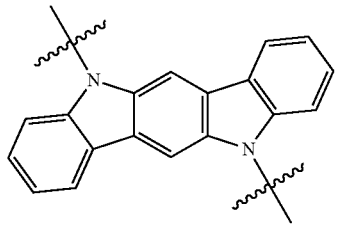

(1.2)

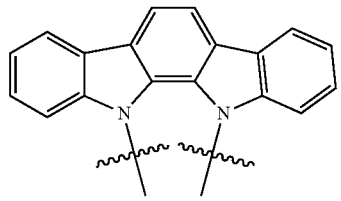

(1.3)

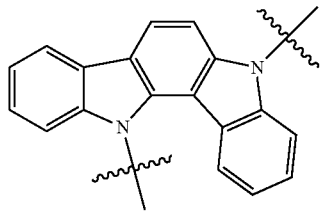

(1.4)

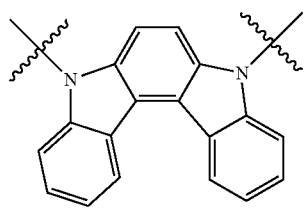

(1.5)

However other indolocarbozole moieties may be employed as well. For example, the indolocarbozole moieties described in U.S. Patent Application Publication No. 20120241732 to Endo et al. may be used.

The following furylpyridine acceptor moieties may be used,

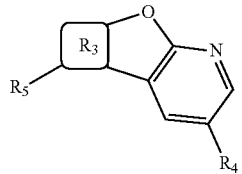

(2)

wherein each furylpyridine moiety is generally represented formula (2), ring $R_3$ is an aromatic ring, $R_4$ and $R_5$ are independently selected from a hydrogen and indolocarbozole, and at least one of $R_4$ and $R_5$ is the indolocarbozole moiety represented by formula (1). For example, the moieties represented by formulae (2.1), (2.2), and (2.3) are specific embodiments of the moiety represented by formula (2):

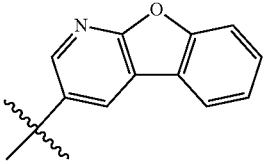

(2.1)

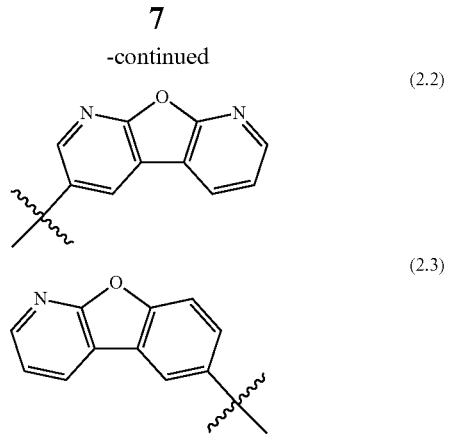

(2.2)

(2.3)

Optionally, the indolocarbozole moiety may be bonded to the moiety shown in formula (3)

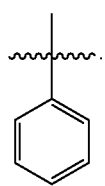

(3)

FIG. 3, depict various embodiments of the inventive compound that have been evaluated for their luminescent properties. FIG. 5 is a table that shows energy calculations associated with the compounds of FIG. 3. Typically, embodiments of the inventive compound exhibits a $\Delta E_{ST}$ of no greater than about 0.25 eV. Preferably, the compound exhibits a $\Delta E_{ST}$ of no greater than about 0.20 eV. Optimally, the compound exhibits a $\Delta E_{ST}$ of no greater than about 0.10 eV.

Figure 4A:
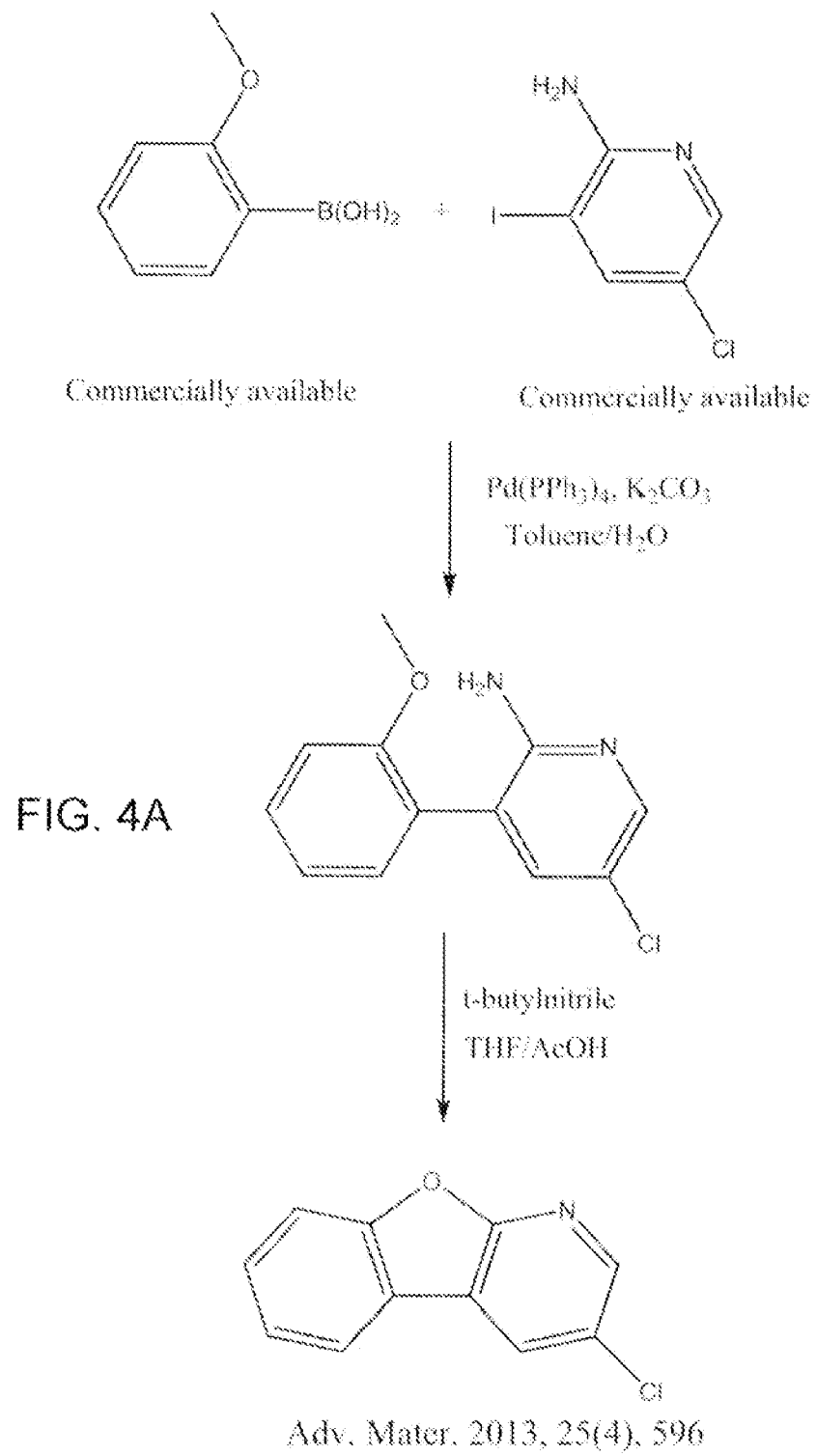

FIG. 4 depicts in step-by-step sequence how an exemplary compound (Compound 9) may be chemically synthesized in a step by step manner. A person of ordinary skill in the art will be able to synthesize any compound of the invention through techniques described in the literature contained in FIG. 4, through other known techniques, or through techniques that may be discovered through routine experimentation.

$\Delta E_{ST}$ and other values shown in FIG. 5 may be arrived at through theoretical calculations and verified via ordinary spectroscopy methods known in the art by persons of ordinary skill in the art.

Electroluminescent Material for OLED

Embodiments of the inventive compound may be used as is, provided in a polymeric form, and/or be incorporated in a matrix material used for OLED applications such as a luminescent display device having an array of pixels. The material may be made to emit red, green, and/or blue light, e.g., through the use of the compound. An additional luminescent and/or TADF compound may be present as well.

An exemplary OLED device may have an architecture shown in FIG. 1. As shown, the device 100 may include a first electrode 25, a second electrode 85, and a luminescent layer 40 interposed and in electronic communication with the first and second electrodes. The first electrode 25 may be comprised of an indium tin oxide layer 10 and a hole-injection layer 20. Typically, the indium tin oxide is both electrically conductive and optically transparent to a degree sufficient to carry out the luminescent layer's intended purpose. Interposed between the first electrode and the luminescent layer 40 is an optional hole-transporting layer 30 Exemplary hole-transporting materials include, e.g., N,N'-Bis(napthalen-1-yl)-N,N'-bis(phenyl)benzidine (NPB), 4,4',4"-tris(N-carbazolyl)-triphenylamine) (TcTa), and Di-[4-(N,N-ditoyl-amino)-phenyl]cyclohexane (TAPC). The second electrode 85 may be comprised of electronically conductive layers 80 and 70, which may be optically transparent or opaque, and an electron-injection layer 60. Materials suitable for use in the electrically conductive layers 80 and 70 include, for example, a metal, an alloy thereof, and/or a compound that exhibit substantially ionic bonding. As shown, layer 80 comprises aluminum and layer 70 comprises LiF. An optional electron-transporting layer 50 may be located between the second electrode 85 and the luminescent layer 40. Exemplary electron-transporting materials include, e.g., 2,2',2"-(1,3,5-Benzinetriyl)-tris(1-phenyl-1-H-benzimidazole) (TPBi) and, 1,3,5-Tris[(3-Pyridyl)-phen-3-yl]benzene (TmPyPb).

The luminescent layer includes the TADF compound. Optionally, the luminescent layer may include an additional compound that may alter the emission spectrum of the luminescent layer. Such compounds may be light emissive and/or absorptive in nature at various wavelengths depending on the desired color or colors.

In operation, a voltage is applied between the first and second electrode. Holes from the hole-injection layer 20 are combined with electrons from the electron-injection layer 70 at the luminescent layer 40. As a result, light is emitted from the luminescent layer 40. Typically, emitted light may travel through the indium tin oxide layer 10.

Thicknesses of the various layers of the inventive device 100 may vary according to techniques used for deposition. Exemplary deposition techniques include evaporation, sputtering, chemical vapor deposition, spin coating, etc.

Figure 6:
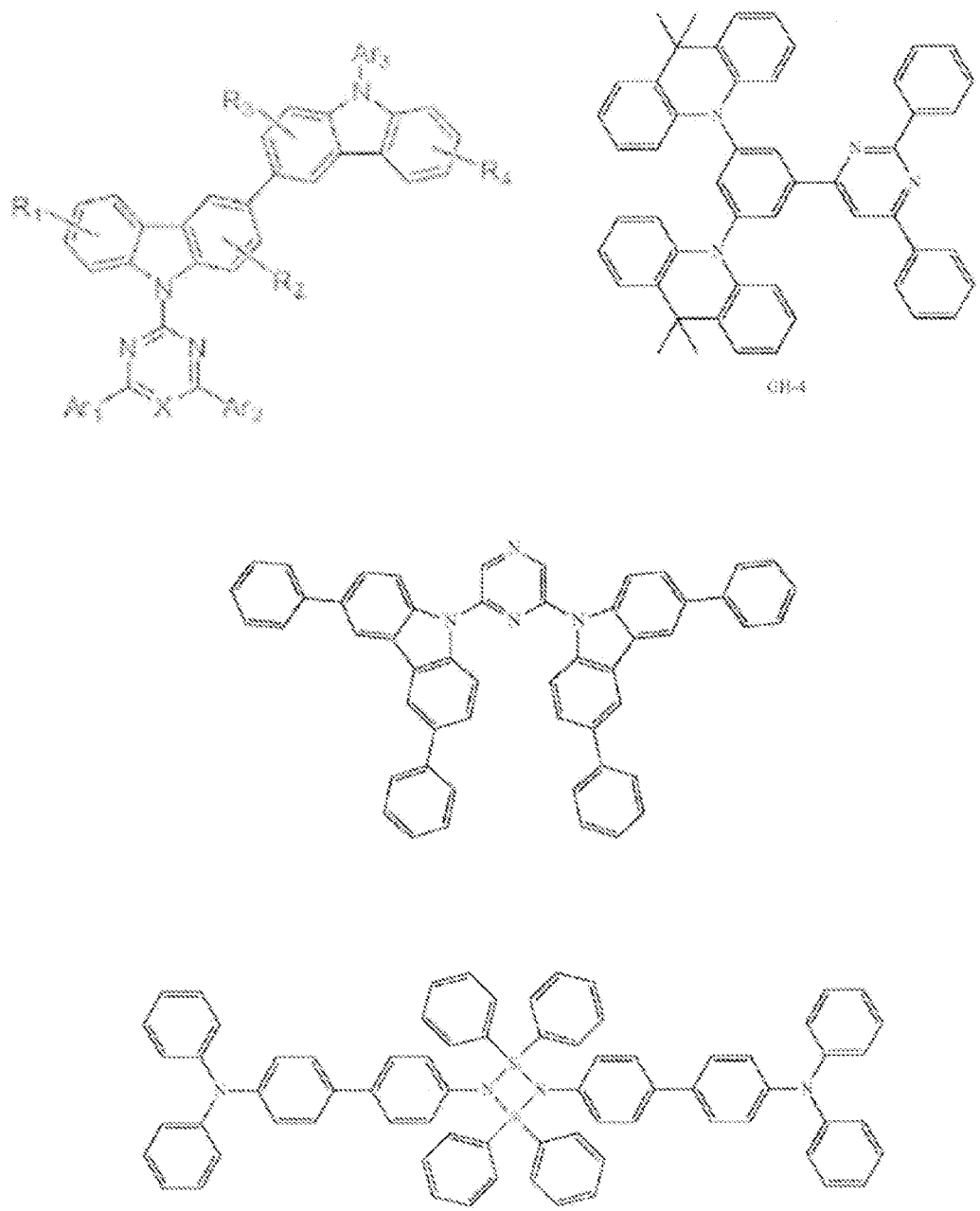
FIG. 6 depicts various electroluminescent compounds having at least one donor moiety and at least one acceptor moiety.

Variations of the present invention will be apparent to those of ordinary skill in the art in view of the disclosure contained herein. For example, while the inventive compound has generally been described in terms of an indolocarbazole moiety bonded to a furylpyridine moiety, the invention does not, strictly speaking, require either moiety in all instances. Donor moieties such as those described in the publications, e.g., published patent applications, cited herein may be used. For example, FIG. 6 depicts various electroluminescent compounds having at least one donor moiety and one acceptor moiety. The donor moieties shown in FIG. 6 may be covalently bonded to least one furylpyridine moiety to form a TADF compound exhibiting a desired $\Delta E_{ST}$.

In addition, while the invention may be used in electroluminescent devices, the invention may not be limited to electroluminescence applications. In addition, emission modifiers, e.g., compounds and/or moieties that modify the emission spectrum the inventive compound, may be included. In such a case, the emission modifier may be itself an electroluminescent or luminescent material. Dyes and the like may also serve as an emission modifier in the luminescent material of the invention.

Furthermore, any particular embodiment of the invention may be modified to include or exclude features of other embodiments as appropriate without departing from the spirit of the invention. For example, the invention may include novel and nonobvious compounds having utility outside luminescence applications.

It is to be understood that, while the invention has been described in conjunction with the preferred specific embodiments thereof, the foregoing description merely illustrates and does not limit the scope of the invention. Numerous alternatives and equivalents exist which do not depart from the invention set forth above. Other aspects, advantages, and modifications within the scope of the invention will be apparent to those skilled in the art to which the invention pertains.

In view of the language capabilities and limitations of the ordinary artisan, the claims that follow this specification may be amended using synonyms and phrasing to describe existing material in the specification that do not appear verbatim in the specification. Similarly, all numbers and ranges herein are to be interpreted to a significant digit that the ordinary artisan would recognize as nontrivial.

All publications mentioned herein are hereby incorporated by reference in their entireties to an extent not inconsistent with the above disclosure.

We claim:

1. A chemical compound of a structure that includes an indolocarbazole moiety covalently bonded to at least one furylpyridine moiety.

2. The compound of claim 1, wherein the indolocarbaezole moiety is bonded via a nitrogen thereof to at least one furylpyridine moiety.

3. The compound of claim 2, wherein the furylpyridine moiety is furylmonopyridine.

4. The compound of claim 2, wherein the furylpyridine moiety is a furylbipyridine.

5. The compound of claim 1, wherein the indolocarbaezole moiety is bonded via nitrogens thereof to furylpyridine moieties.

6. The compound of claim 1, wherein

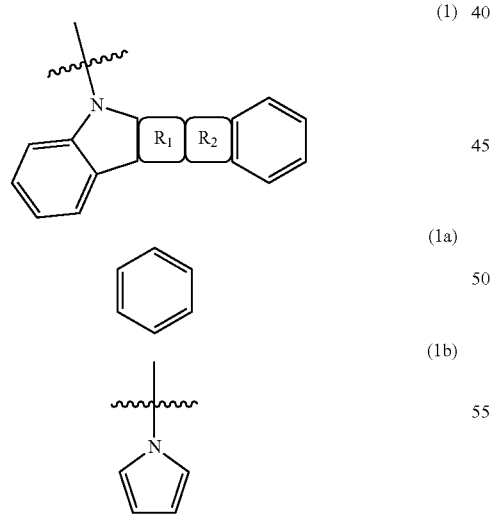

the indolocarbazole moiety is represented by formula (1),
ring $R_1$ is represented by formula (1a) and is fused to an adjacent heterocycle,
ring $R_2$ is represented by formal (1b) and is fused to an adjacent aromatic ring, and
rings $R_1$ and $R_2$ are fused together.

7. The compound of claim 6,

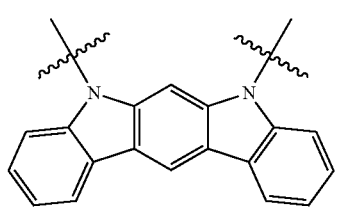

(1.1)

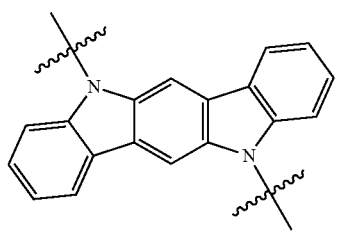

(1.2)

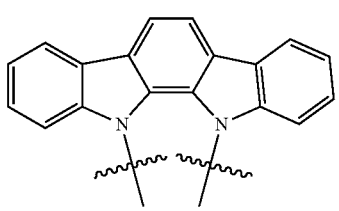

(1.3)

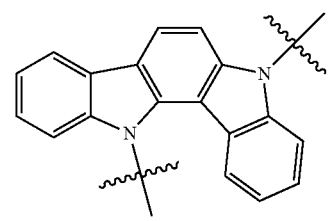

(1.4)

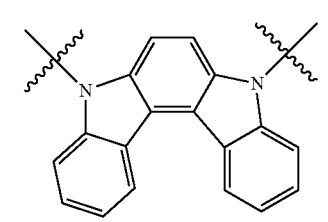

(1.5)

wherein the indolocarbazole moiety is represented by one of formulae (1.1), (1.2), (1.3), (1.4), and (1.5).

8. The compound of claim 6, wherein

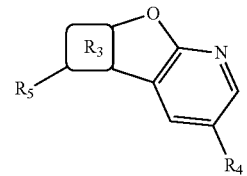

(2)

each furylpyridine moiety is represented formula (2),
ring $R_3$ is an aromatic ring,
$R_4$ and $R_5$ are independently selected from a hydrogen and indolocarbaezole, and at least one of $R_4$ and $R_5$ is the indolocarbaezole moiety represented by formula (1).

9. The compound of claim 8,

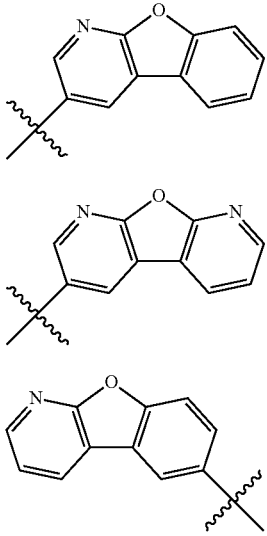

wherein each furylpyridine moiety is represented by one of formulae (2.1), (2.2), and (2.3).

10. The compound of claim 6,

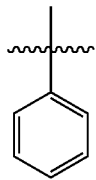

wherein one of the nitrogens of the indolocarbazole moiety is bonded to an aromatic moiety represented by formula (3).

11. A luminescent material comprising the compound of claim 1.

12. The luminescent material of claim 11, wherein the material is capable of emitting blue light.

13. The luminescent material of claim 11, wherein the material is capable of emitting green light.

14. The luminescent material of claim 11, wherein the material is capable of emitting red light.

15. The luminescent device, comprising the material of claim 11.

16. The device of claim 15, wherein the compound exhibit a $\Delta E_{ST}$ of no greater than about 0.25 eV.

17. The device of claim 15, wherein the compound exhibits TADF.

18. The device of claim 15, wherein the compound is in electronic communication with hole-injection and electron-injection electrodes.

19. The device of claim 18, wherein at least one electrode comprises an optically transparent material.

20. The device of claim 18, wherein the optically transparent material is an electronically conductive metallic oxide.

21. The device of claim 18, wherein the electronically conductive metallic oxide includes tin and/or indium.

22. A thermally activated delayed fluorescent compound of a structure that includes a donor moiety covalently bonded to at least one furylpyridine acceptor moiety, wherein the compound exhibits a $\Delta E_{ST}$ of no greater than about 0.25 eV.

23. The compound of claim 22, wherein the donor moiety is an indolocarbazole moiety.

24. A luminescent material comprising the compound of claim 22.

25. An electroluminescent device containing the material of claim 24.

* * * * *